(12) United States Patent
Hesketh et al.

(10) Patent No.: US 6,881,832 B1
(45) Date of Patent: Apr. 19, 2005

(54) EXPRESSION SYSTEM FOR THE SECRETION OF INTRACELLULAR PROTEINS

(75) Inventors: John Edward Hesketh, Newcastle (GB); Albert Tauler, Barcelona (ES); Ian Fraser Pryme, Bergen (NO)

(73) Assignee: UNI Targeting Research AS, Bergen (NO)

( * ) Notice: Subject to any disclaimer, the term of this patent is extended or adjusted under 35 U.S.C. 154(b) by 0 days.

(21) Appl. No.: 09/518,190

(22) Filed: Mar. 2, 2000

Related U.S. Application Data

(63) Continuation of application No. PCT/GB98/02664, filed on Sep. 4, 1998.

(30) Foreign Application Priority Data

Sep. 5, 1997 (GB) .............................................. 9718908

(51) Int. Cl.$^7$ .......................... C07H 21/04; C12P 21/06; C12N 1/20; C12N 15/00; C12N 15/74

(52) U.S. Cl. .................. 536/23.5; 435/69.1; 435/252.3; 435/320.1; 435/471

(58) Field of Search ........................ 536/23.5; 530/402; 435/69.1, 70.1, 71.1, 71.2, 252.3, 320.1, 471

(56) References Cited

FOREIGN PATENT DOCUMENTS

| EP | 0 226 057 A3 | 5/1988 |
|---|---|---|
| EP | 0 266 057 A2 | 5/1988 |
| EP | 0 279 582 A3 | 8/1988 |
| EP | 0 279 582 A2 | 8/1988 |
| WO | WO 91/13151 | 9/1991 |
| WO | WO 93/04165 | 3/1993 |

OTHER PUBLICATIONS

Scott FL et al. J. Biol. Chem. 271(3):1605–1612, 1996.*
Sleep D et al. (Biotechnology 8(1):42–46, 1990.*
Kordula T., et al. Biochem J. 293:187–193, 1993.*
Smith DB and Johnson KS. Gene 67:31–40, 1988.*
Demolder, J., et al., "Efficient synthesis of secreted murine interleukin–2 by Saccharomyces cerevisiae: influence of 3'–untranslated regions and codon usage," Elsevier Science Publishers B. V., Gene 111 207–213, (1992).
Yang, C., et al., "The Expression and Characterization of Human Recombinant Proinsulin–Like Growth Factor II and a Mutant That Is Defective in the O–Glycosylation of Its E Domain," Endocrinology USA 137:2766–2773, The Endocrine Society, (1996).
Lia, Y., et al., "Processing of fusion protein by endoprotease in COS–1 cells for secretion of mature peptide by using a chimeric expression vector," Proc. Natl. Acad. Sci. USA 90:8957–8961, National Academy Science, (1993).
Aviv, H. et al., "Biosynthesis and Stability of Globin mRNA in Cultured Erythroleukemic Friend Cells," Cell 8:495–503 (1976).
Blobel, G. and Dobberstein, B., "Transfer of Proteins Across Membranes: I. Presence of Proteolytically Processed and Unprocessed Nascent Immunoglobuin Light Chains On Membrane–Bound Ribosomes of Murine Myeloma," J. Cell Biol. 67:835–851 (1975).
Bock, S.C. et al., "Cloning and expression of the cDNA for human antithrombin III," Nucl. Acids Res. 10:8113–8125 (1982).
Bonnieu, A. et al., "Sequence Determinants of c–myc mRNA Turn–over: Influence of 3' and 5' Non–coding Regions," Oncogene Res. 3:155–166 (1988).
Bonnieu, A. et al., "AUUUA motifs are dispensable for rapid degradation of the mouse c–myc RNA," Oncogene 5:1585–1588 (1990).
Devlin, J. et al., "Expression of Granulocyte Colony–Stimulating Factor by Human Cell Lines," J. Leukoc. Biol. 41:302–306 (1987).
Garcia, C.K. et al., "Molecular Characterization of a Membrane Transporter for Lactate, Pyruvate, and Other Monocarboxylates: Implications for the Cori Cycle," Cell 76:865–873 (1994).
Hesketh, J. et al., "Targeting of c–myc and β–globin coding sequences to cytoskeletal–bound polysomes by c–myc 3' untranslated region," Biochem. J. 298:143–148 (1994).
Hesketh, J.E., "Intracellular Sorting of Macromolecules," Biochem. Soc. Trans. 24:521–527 (1996).
Hovland, R. et al., "The mRNAs for cyclin A, c–myc and ribosomal proteins L4 and S6 are associated with cytoskeletal–bound polysomes in HepG2 cells," Biochem. J. 310:193–196 (1995).
Hovland, R. et al., "The Compartmentalization of Protein Synthesis: Importance of Cytoskeleton and Role in mRNA Targeting," Int. J. Biochem. Cell Biol. 28:1089–1105 (1996).
Huang, Z.–M. and Yen, T.S.B., "Hepatitis B Virus RNA Element That Facilitates Accumulation of Surface Gene Transcripts in the Cytoplasm," J. Virol. 68:3193–3199 (1994).
Kim, Y.–J. et al., "Molecular Cloning and Expression of Human Galβ1,3GalNAc α2,3–Sialytransferase (hST3Gal II)," Biochem. Biophys. Res. Commun. 228:324–327 (1996).
Kislauskis, E.H. et al., "Sequences Responsible for Intracellular Localization of β–Actin Messenger RNA Also Affect Cell Phenotype," J. Cell Biol. 127:441–451 (1994).

(Continued)

Primary Examiner—Brenda Brumback
Assistant Examiner—Robert S. Landsman
(74) Attorney, Agent, or Firm—Sterne, Kessler, Goldstein & Fox P.L.L.C.

(57) ABSTRACT

Mammalian signal peptides can be used to aid in the secretion of mammalian proteins that are normally not secreted. By inactivating signals normally present in the 3' UTRs of mRNAs encoding proteins that are normally not secreted from mammalian cells, the proportion of such mRNA molecules directed to free and cytoskeletal bound polysomes can be reduced.

20 Claims, 4 Drawing Sheets

OTHER PUBLICATIONS

Figure 1:
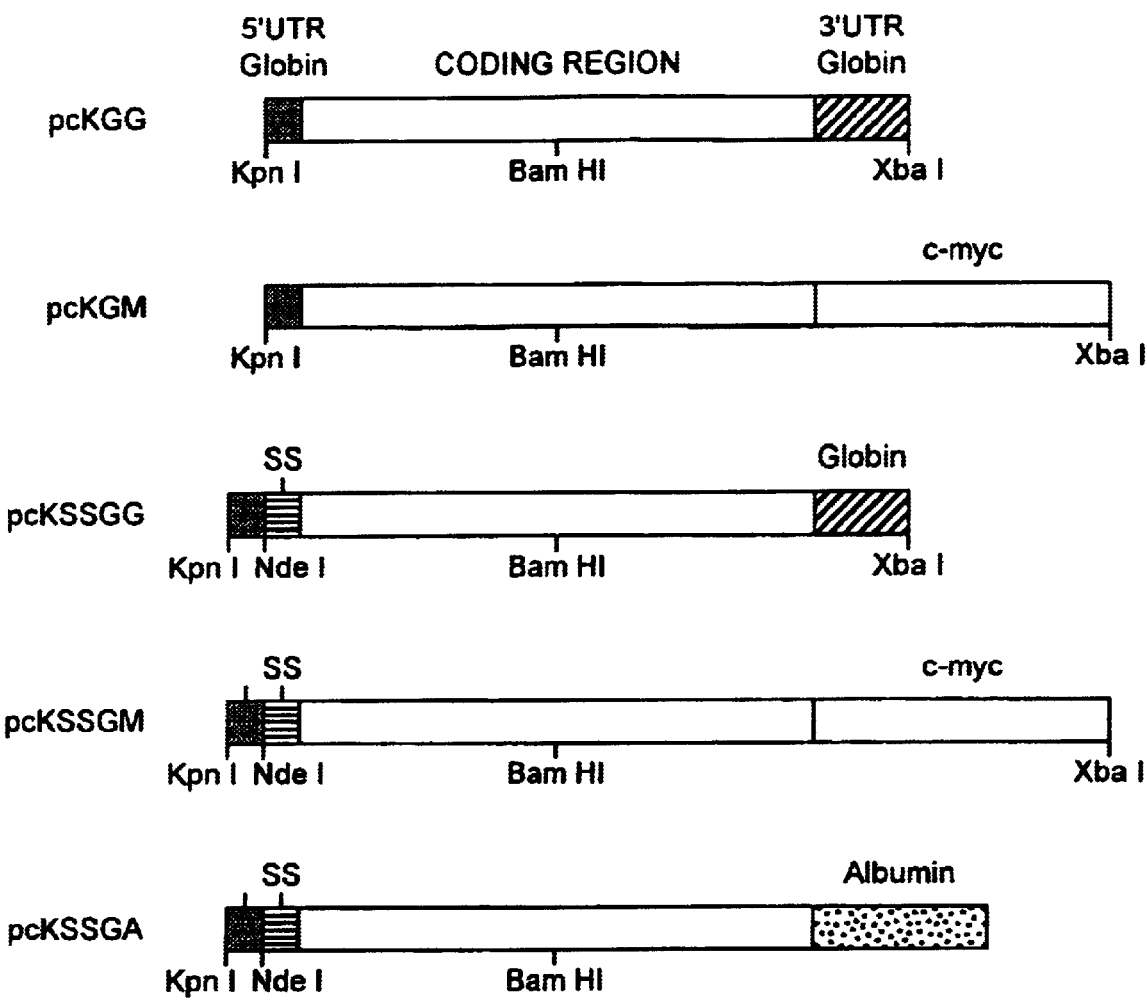

Lee, Y.-C. et al., "An Efficient Expression Vector for Extracellular Secretion in Mammalian Cells," *Mol. Cells* 6:552–556 (1996).

Lin, F.-K. et al., "Monkey erythropoietin gene: cloning, expression and comparison with the human erythropoietin gene," *Gene 44*:201–209 (1986).

Maeda, Y. et al., "Efficient Production of Active TNF By Albumin Signal Peptide," *Biochem. Mol. Biol. Int.* 42:825–832 (1997).

Mahon, P. et al., "Localisation of metallothionein isoform mRNAs in rat hepatoma (H4) cells," *FEBS Lett. 373*:76–80 (1995).

Michel, M.-L. et al., "Expression of Amplified Hepatitis B Virus Surface Antigen Genes in Chinese Hamster Ovary Cells," *Bio/Technology 3*:561–566 (1985).

Pryme, I.F. et al., "Compartmentation of the Protein Synthetic Machinery of CHO Cells into Free, Cytoskeletal-bound and Membrance–bound Polysomes," *The Genetic Engineer and Biotechnologist 16*:137–144 (1996).

Shak, S. et al., "Recombinant human DNase I reduces the viscosity of cystic fibrosis sputum," *Proc. Natl. Acad. Sci. USA 87*:9188–9192 (1990).

Vedeler, A. et al., "The characterization of free, cytoskeletal and membrane–bound polysomes in Krebs II ascites and 3T3 cells," *Mol. Cell. Biochem. 100*:183–193 (1991).

Veyrune, J.-L. et al., "A localisation signal in the 3' untranslated region of c–myc mRNA targets c–myc mRNA and β–globin reporter sequences to the perinuclear cytoplasm and cytoskeletal–bound polysomes," *J. Cell Sci. 109*:1185–1194 (1996).

Wilson, I.A. et al., "Differential localization of the mRNA of the M and B isoforms of creatine kinase in myoblasts," *Biochem. J. 308*:599–605 (1995).

Zambetti, G. et al., "Targeting of a chimeric human histone fusion mRNA to membrane–bound polysomes in HeLa cells," *Proc. Natl. Acad. Sci. USA 84*:2683–2687 (1987).

* cited by examiner

EXPRESSION SYSTEM FOR THE SECRETION OF INTRACELLULAR PROTEINS

This application is a continuation of the international application, PCT/GB98/02664, filed Sep. 4, 1998 and published as WO 99/13090, which claims priority benefit to British application no. GB 9718908.8, filed Sep. 5, 1997, the full disclosures of which are herein incorporated by reference.

The present invention relates to the secretion of proteins from mammalian cells.

Mammalian cell lines are increasingly being used to produce commercially significant amounts of recombinant proteins in cell factories and in transgenic animals. There are numerous examples where normally secreted proteins are being produced in this way (Bock et al 1982, Michel et al 1985, Lin et al 1986, Devlin et al 1987, Shak et al 1990), as well as a number of commercial vectors for the secretion of heterologous proteins. However such systems have been largely used for the production of secreted proteins rather than proteins which are normally intracellular and secretion of intracellular proteins in mammalian expression systems is an increasingly important aim in biotechnological research (James and Simpson, 1996). The present inventors are only aware of one paper describing the successful secretion of an intracellular protein from mammalian cells (Lee et al, 1996). This protein (sialyltransferase), however, is normally synthesised in the endoplasmic reticulum (ER) and successful secretion did not depend on an initial redirection of the mRNA.

It is well established that specific mRNAs are translated in specific subcellular locations, for instance membrane and secreted proteins are translated on the rough endoplasmic reticulum in association with membrane-bound polysomes (Blobel and Dobberstein, 1975), and the mRNAs for proteins such as c-myc (Hesketh et al, 1994, metallothionein I (Mahon et al 1995), ribosomal proteins and cyclin A (Hovland et al, 1995) are translated in association with cytoskeletal-bound polysomes (for reviews see Hesketh 1996, Hovland et al 1996). It now appears that the protein synthetic apparatus is compartmentalised into at least three polysome populations—free (FP), cytoskeletal-bound (CBP) and membrane-bound (MBP) polysomes. These different populations of mRNAs can be separated using a sequential detergent/salt extraction (Vedeler et al 1991). Different signals direct these mRNAs to their site for translation. In the case of membrane and secreted proteins it has been well established that the signal peptide is required to target the ribosome-mRNA complex to the endoplasmic reticulum whilst recent evidence has shown that for mRNAs localised in the cytoplasm or associated with the cytoskeleton there are signals in the 3'untranslated region (Kislauskis et al 1994, Hesketh et al 1994, Wilson et al 1995, Veyrune et al 1996).

According to the present invention there is provided an RNA molecule encoding a mammalian signal peptide operatively linked to a protein that would normally not be secreted from a mammalian cell, said signal peptide allowing at least some of said protein to be synthesised on the endoplasmic reticulum in a manner so that it can be secreted from said mammalian cell.

Without being bound by theory, it is believed that the signal peptide is provided initially and then translation of the mRNA stops or slows down to allow the signal peptide to bind to a signal recognition particle and direct ribosomes associated with the mRNA to the endoplasmic reticulum. Translation then starts again/speeds up to allow the rest of the protein to be translated.

The term "protein" is used herein in a broad sense to include moieties comprising amino-acids linked by peptide bonds. It therefore includes peptides and polypeptides.

The present invention is widely applicable. In principle the sequence of any naturally occurring mammalian signal peptide that is normally associated with a protein secreted from mammalian cells can be used to design appropriate RNA molecules encoding a mammalian signal peptide for use in the present invention.

Variants of such naturally occurring signal peptides that can be used to secrete such a protein may also be used and, for the purposes of the present invention, are deemed to be within the scope of the term "mammalian signal peptide". Preferred such variants have at least at least 50% amino acid sequence identity with naturally occurring mammalian signal peptide sequences. More preferably the degree of sequence identity is at least 75%. Sequence identities of at least 90% or of at least 95% are most preferred. For the purposes of the present invention sequence identity can be determined by using the "BESTFIT" program of the Wisconsin Sequence Analysis Package GCG 8.0.

Preferred signal peptide sequences include: rat albumin (Database Accession Number J00698), bovine growth hormone, lactalbumin and other milk proteins.

A skilled person is able to ascertain the signal sequences of many proteins from available database sequences or publications. Even if these sequences are not published, for example, sequence homology studies may be used to compare a candidate amino-acid sequence with amino acid sequences of known signal sequences.

In a preferred embodiment of the present invention the RNA molecule does not include a sequence that might direct the molecule to an intracellular location other than the endoplasmic reticulum or to free and/or to cytoskeletal bound polysomes, or it includes such a sequence but in a form that is modified to reduce its effectivity in directing molecules to an intracellular location other than the endoplasmic reticulum or to free and/or to cytoskeletal bound polysomes (relative to the corresponding naturally occurring sequence).

In this preferred embodiment of the present invention possible competition between a signal sequence directing a protein to the endoplasmic reticulum and an RNA sequence directly RNA encoding the protein to an intracellular location other than the endoplasmic reticulum or to free and/or to cytoskeletal bound polysomes can be avoided, or at least altered so as to increase the probability of proteins being directed to the endoplasmic reticulum.

This can be achieved by providing the RNA molecule with a deletion, insertion or substitution in respect of all or part of a 3' untranslated (UTR) region relative to the corresponding region present in naturally occurring RNA encoding the protein that would normally not be secreted from a mammalian cell. Signals present in 3'UTR regions of RNA molecules directed to specific subcellular locations or to free or cytoskeletal—bound polysomes are believed to control the localisation of such mRNAs, at least to some degree and mutations in such regions can inactivate the signals. The signals in the 3' UTR regions of RNA molecules can be identified by deletion or mutation of sequences within the 3'UTR region of said mRNA molecules and assay of localisation capabilities by linking to a reporter gene and transfection into mammalian cells in culture followed by hybridisation assays to detect mRNA distribution.

DNA molecules capable of being transcribed to provide the RNA molecules discussed above are also within the scope of the present invention. They may be provided in the form of a vector (e.g. a plasmid, phage or cosmid), although this is not essential.

Also within the scope of the present invention is a mammalian cell comprising a DNA or RNA molecule as described above. The mammalian cell may be present in cell culture or in a non-human animal. The term "cell culture" is used herein to mean one or more cells that are not present in an animal and that can be used to express proteins under appropriate conditions. Usually such cells will be maintained in an appropriate growth medium under buffered conditions. The cell culture may be e.g. a culture of mammalian fibroblasts, a CHO, BHK or myeloma cell culture. The non-human animal may be a transgenic animal. (The term "transgenic animal" includes transkaryotic animals.) It may secrete heterologous proteins in its milk.

The present invention also includes a method obtaining a protein from a mammalian cell comprising the step of expressing the protein using a nucleic acid molecule of the present invention and allowing the cell to secrete the protein. The protein may then be purified by known purification techniques.

A chimaeric protein comprising a mammalian signal sequence linked to a protein that would normally not be secreted from a mammalian cell is another aspect of the present invention. Such a protein can be produced by translating an RNA molecule of the present invention.

In addition to the other aspects of the present invention, it should be noted that the present invention provides nucleic acid molecules that hybridise to the nucleic acid molecules discussed above. These may be useful e.g. as probes, as primers, or as antisense molecules for use in altering expression, etc.

Desirably such hybridising nucleic acid molecules are at least 10 nucleotides in length and preferably are at least 25 or at least 50 nucleotides in length. They may hybridise under stringent hybridisation conditions. One example of stringent hybridisation conditions is where attempted hybridisation is carried out at a temperature of from about 35° C. to about 65° C. using a salt solution which is about 0.9 molar. However, the skilled person will be able to vary such parameters as appropriate in order to take into account variables such as probe length, base composition, type of ions present, etc.

Although the present invention has been described above largely with reference to naturally occurring mammalian signal peptides or variants thereof, in its broadest scope all signal peptides capable of functioning in mammalian cells may be used. These may be naturally or non-naturally occurring. Preferably (but not essentially) they do not occur naturally in prokaryotic organisms (e.g. *E. coli*).

The present invention will now be described by way of example only with reference to the accompanying figures, wherein FIG. 1 shows a schematic diagram of the constructs described in the Material and Methods. The parent vector is pcDNA3. The solid square represents the native 5'UTR of rabbit beta-globin. SS is the rat albumin signal sequence.

Figure 2:
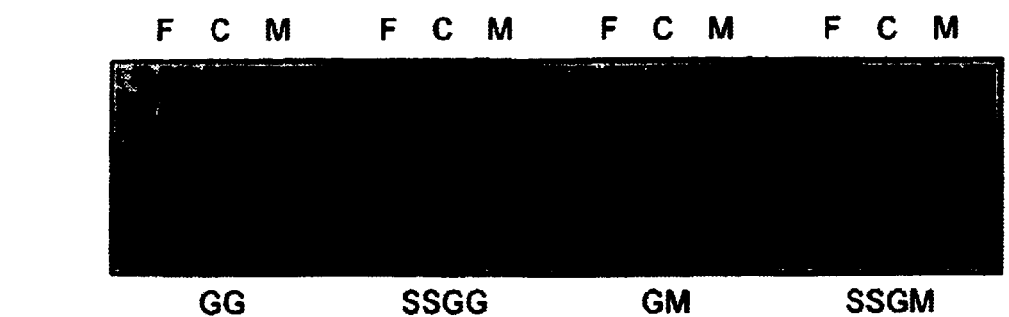

FIG. 2 shows a Northern Hybridisation of total RNA from polysomes isolated from transfected cells. All lanes were loaded with 10 $\mu$g RNA; the filter was hybridised with a rabbit beta-globin cDNA probe and specific bands detected by autoradiography at −70° C. for 3 days using Hyperfilm-MP, F, free polysomes; C, cytoskeletal-bound polysomes; M, membrane-bound polysomes.

Figure 3:
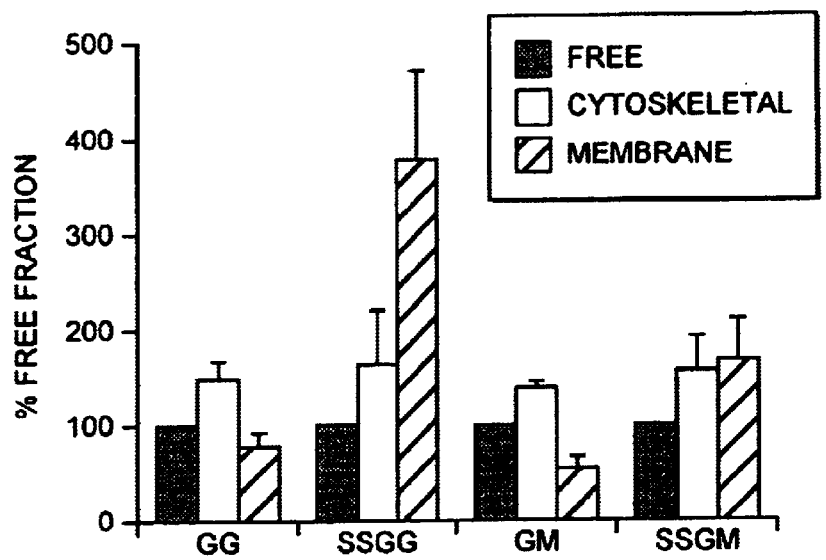

FIG. 3 shows a quantification of the distribution of globin mRNA in transfected cells. Results are expressed in arbitrary units mRNA per unit 18S rRNA obtained from direct radioactivity imaging using a Canberra Packard Instantimager. Abundance values were normalised taking the abundance in free polysomes as 100 for each experiment. Results are means±S.E.M (n=4). Groups were compared using Students 't' test: transcript abundance in the membrane-bound polysomes was significantly different between GG and SSGG cells (p=0.01), GM and SSGM (p<0.05) using a two-tailed test and between SSGM and SSGG using a one-tailed test.

Figure 4:
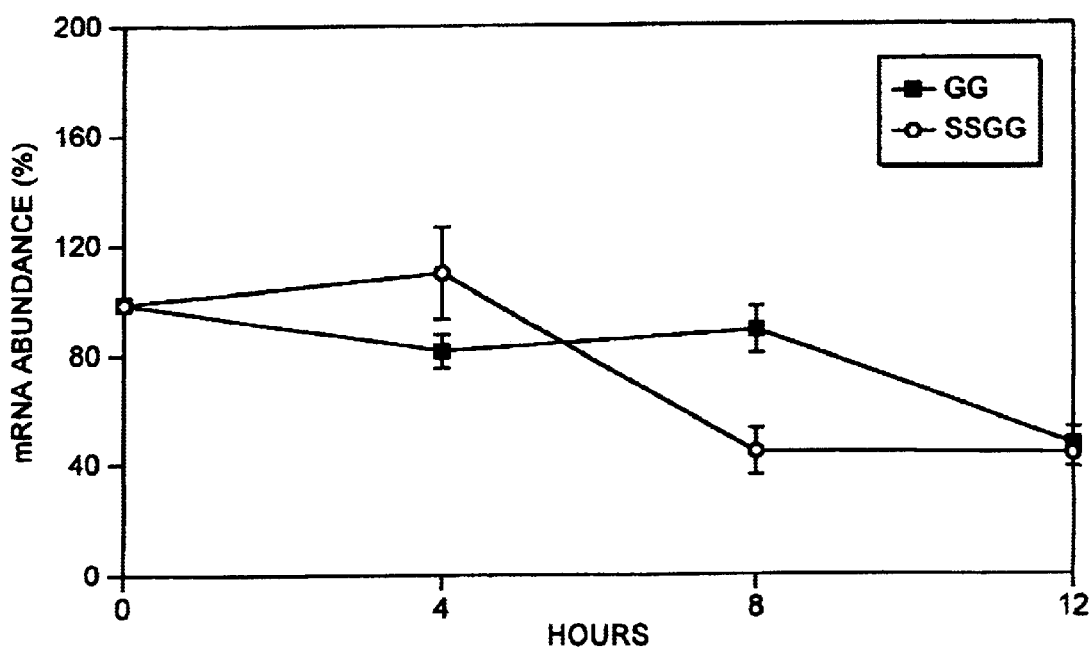

FIG. 4 shows the mRNA stability of the transcripts. Cells were grown to 70% confluence and transcription inhibited with Actinomycin D. RNA was extracted at time points then analysed by Northern Blotting. Quantification was carried out by direct radioactivity imaging using a Canberra Packard Instantimager. Results are means±S.E.M and are expressed as a percentage of initial abundance.

GG and SSGG (n=6)

Figure 5:
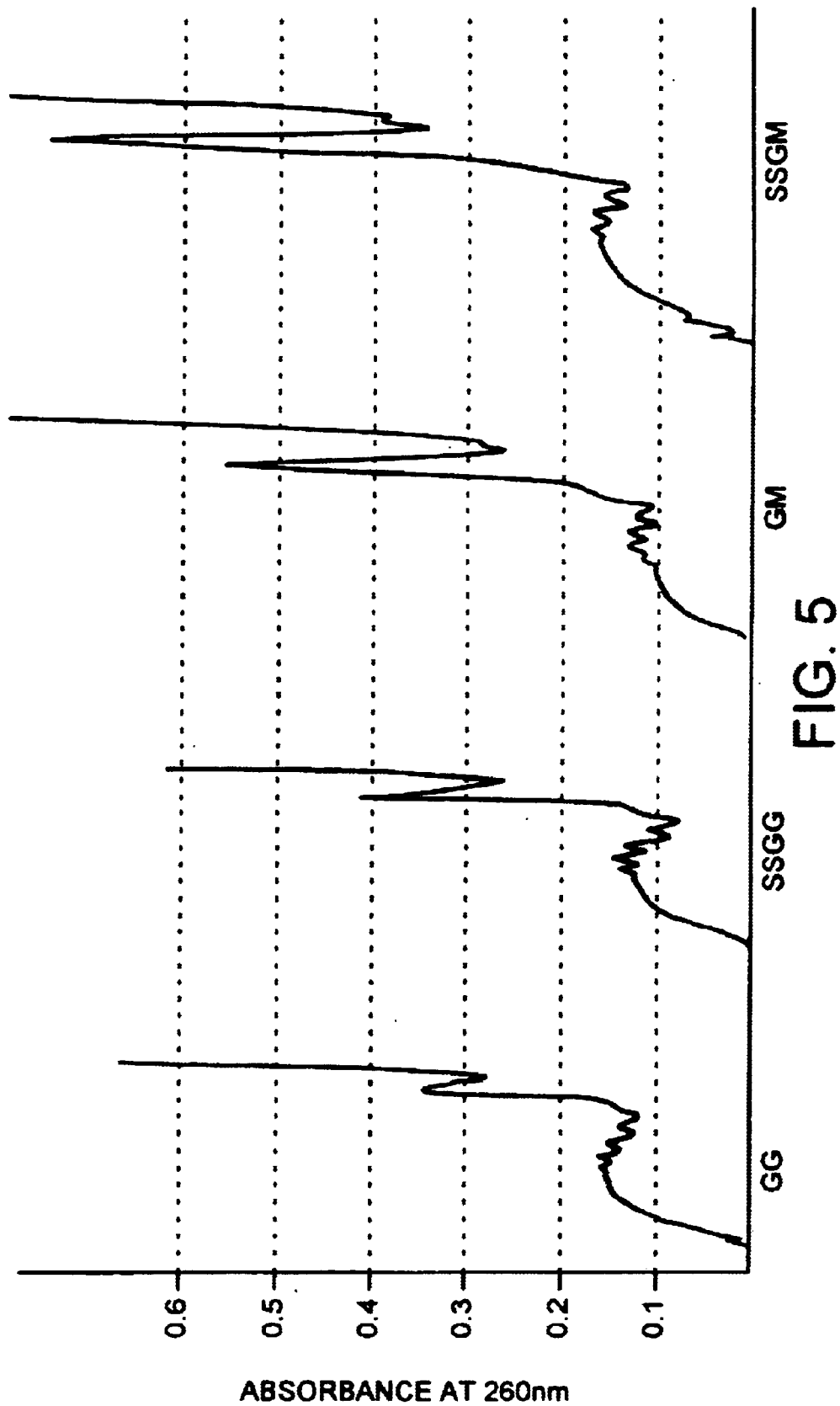

FIG. 5 shows polysome profiles of transfected Ltk− cells. Soluble detergent/salt extracted material was layered on to a 15%–40% sucrose gradient and centrifuged at 200 000×g for 1 hour. Polysome profiles were monitored by measuring the absorbance at 260 nm using a flow cell.

FIG. 6 shows a Northern Hybridisation and quantification of SSGA.

Figure 6A:
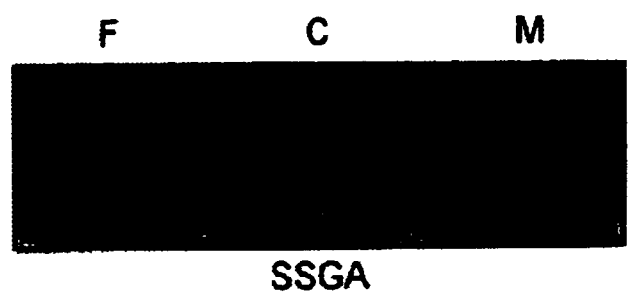

FIG. 6A: Northern Hybridisation of Ltk− cells transfected with pcKSSGA. All lanes were loaded with 20 ug RNA. The filter was hybridised with a rabbit beta-globin cDNA probe.

Figure 6B:
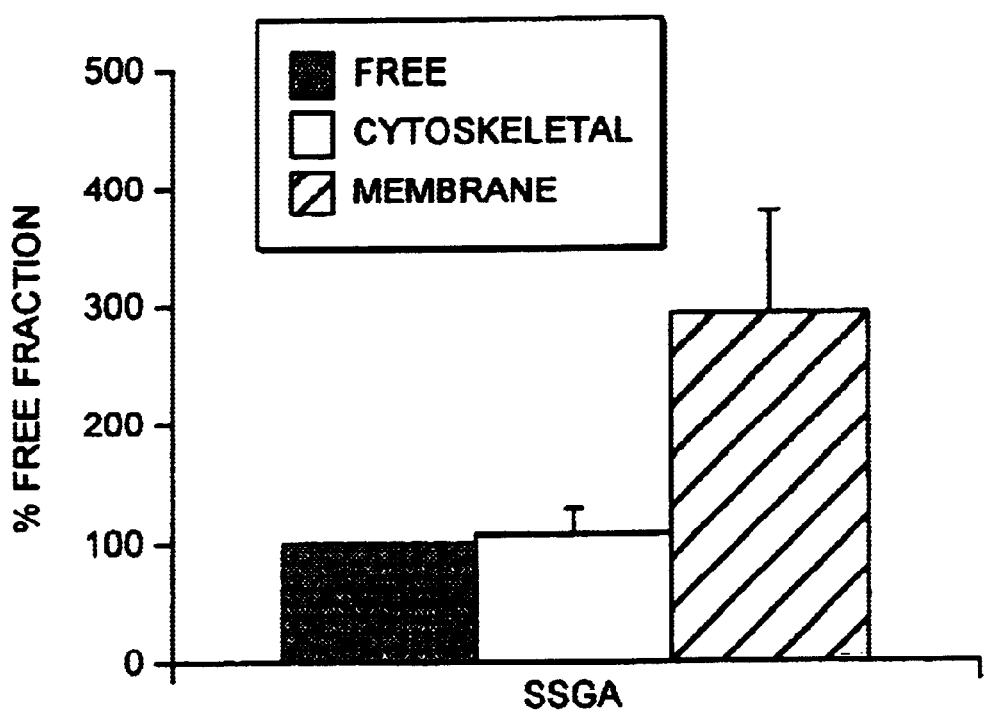

FIG. 6B: Quantification of mRNA abundance.

Results are expressed in arbitrary units of mRNA abundance per unit 18S rRNA obtained from direct radioactivity imaging and normalised by taking the abundance in free polysomes at 100 for each experiment. Results are means±S.E.M. (n=3).

EXAMPLES

The approach taken involved three stages: to construct a series of vectors with the albumin signal peptide and different 3'untranslated region (3'UTR) sequences linked to the rabbit beta-globin 5' untranslated region and coding sequence as a reporter gene; to introduce these constructs into cells by stable transfection and then to determine the subcellular location of the mRNA, and its stability and translational efficiency.

Materials and Methods

Bacteria and cell culture: Plasmids were cloned and propagated in a standard manner. CHO K1 cells were grown in Ham's F12 medium and Ltk− cells, a mouse fibroblast line, were grown in Dulbecco's minimal Eagle's medium. Media were supplemented with 10% foetal calf serum and grown in an atmosphere of 5% $CO_2$. Cells were propagated in 90 mm Petri dishes for fractionation and in 35 mm Petri dishes for transfection.

Vector construction: All constructs (FIG. 1) were derived from rabbit β-globin coding sequences by PCR cloning with the primers described in Table 1 and all contained the native globin 5' UTR. Each construct was verified by sequencing using an ABI 373A sequencer and cycle sequencing. The construction of pcKGG, a plasmid expressing rabbit beta-globin with native 5' and 3' UTRs has been described previously (Mahon et al, 1997). pcKGM expresses globin with the 3'UTR of mouse c-myc and was made as follows. A portion of the globin coding region and the entire c-myc 3'UTR was amplified by PCR using primers KP4 and KP5, KP4 maintaining a BamHI site in the globin coding region and KP5 creating an XbaI site downstream of the c-myc poly-A signal, and plasmid MP13 as template (Veyrune et al 1996). Using 1 ng template and 20 pmol each primer in 1.5 mM $MgCl_2$ and 4 Units Taq Polymerase (PerkinElmer), the reaction was cycled at 94 C for 1 min, 55 C for 1 min, and 72 C for 2 mins. The fragment and pcKGG were digested with BamHI and KpnI and ligated using standard methods (Sambrook et al 1989).

Making the signal sequence constructs required creation of an appropriate restriction site at the AUG codon. This was accomplished by PCR using primers KP6 and KP7; KP6 matching the sequence of pcDNA3 at position 731 and KP7 creating an NdeI site while maintaining the AUG and reading frame. The template was pcKGG, the reaction was with the conditions described above. The product of the reaction was purified, then 5 µg was used in a PCR megaprime with primer KP8 (covering a sequence in the globin coding region which includes a BamHI site), 1 µg pcKGG as the template and the cycles as described above. The resulting fragment was subcloned into pBluescript in the KpnI and BamHI sites, creating pBS-Nde.

The signal sequence was provided by annealing synthetic oligodeoxynucleotides that corresponded to the rat albumin signal sequence (SS1 and SS2). The insert was ligated into the NdeI site of pBS-Nde, creating pBS-SS. The KpnI-BamHI fragment from pBS-SS covering the 5' UTR, albumin signal sequence and globin coding region to the BamHI site, was then ligated into appropriately digested pcKGG and pcKGM to create pcKSSGG and pcKSSGM.

The albumin 3'UTR was removed from the rat albumin gene by restriction and after treatment of the restricted globin vector with Vent polymerase the albumin 3'UTR was introduced by blunt-ended ligation. pcKSSGA was constructed as described for pcKSSGG and pcKSSGM.

Transfection: Transfections were carried out with LipofectAMINE™ (Gibco) according to the manufacturer's instructions. Cells were subcultured on to 35 mm Petri dishes at a density of $5 \times 10^5$ cells/dish and grown to 70–80% confluence. The cells were overlaid with 1 µg of plasmid DNA and 6–10 µl LipofectAMINE in serum-free medium. After 5 hours, serum was added to 10% final concentration. At 24 hours the medium was replaced with complete medium and selection with 200 µg/ml G418 was begun at 72 hours. Cells were maintained in 100 µg/ml G418 once stably transfected. The cell lines are named for the transfected construct, e.g. the cells transfected with pcKGG is called GG, etc.

Cell Fractionation: Ltk– cells were grown to 70% confluence, harvested using a rubber policeman and fractionated by a sequential detergent/salt extraction procedure (Vedeler et al, 1991; Hesketh et al 1994). Polysomes were separated from monosomes and lighter ribonucleoprotein particles by centrifugation at 32,000 g for 17 hours through a 15 ml cushion of 40% sucrose (Hovland et al, 1995).

RNA Extraction and RNA Gel Electrophoresis: Total RNA was extracted by the acid/guanidinium/phenol/chloroform method of Chomczynski and Sacchi (1987), and the preparations were assessed by the A260/A280. RNA was then separated by electrophoresis through a denaturing 2.2 M formaldehyde, 1.2% agarose gel (Sambrook et al 1989) and transferred to a nylon membrane (Genescreen, NEN Dupont, Ltd) by capillary blotting. RNA was fixed to the membrane by UV light and stored dry.

Northern Hybridisation and DNA Probes: Membranes were pre-hybridised at 42 C for a minimum of 6 hours with 0.1 mg/ml denatured salmon sperm DNA in 50% formamide, 10% dextran sulphate, 0.2% bovine serum albumin, 0.2% polyvinylpyrrolidone, 0.2% Ficoll, 0.1% sodium pyrophosphate, 1% SDS and 50 mM Tris HCl, pH 7.5. The beta-globin cDNA probe was described previously (Veyrune et al 1996). The c-myc probe was a cDNA of the 3 exons of the murine gene (Hesketh et al, 1994) and was the gift of Dr. M. Cole (Princeton University, New Jersey USA), the glyceraldehyde-3-phosphate dehydrogenase (GAPDH) probe was a 0.78 kb PstI-XbaI fragment from the human cDNA (American Tissue Culture Collection, accession number 57090) and the 18S rRNA probe was a 1.4 kb BamHI fragment from the cDNA obtained from Dr. R. Fulton, Beatson Institute, Glasgow. 20–30 ng of probe was labelled with $32^P$ dCTP by random priming (Megaprime kit from Amersham International UK). The labelled probe was added to the pre-hybridisation mix and hybridised overnight at 42° C. The filters were washed briefly at room temperature in 2×SSC to remove hybridisation mix. Washes at 65° C. were probe specific as follows: globin-1×SSC, 0.5% SDS 2×30 min., c-myc-0.5×SSC, 1% SDS 2×1 hr., GAPDH-1×SSC, 1% SDS 2×1 hr., 18S-0.2×SSC, 1% SDS. A final brief wash in 0.1×SSC removed SDS. Specific hybridisation was detected and quantified on a Canberra Packard Instantimager. The amounts of specifically bound probe was corrected for non-specific binding and the data expressed per unit of rRNA as measured by hybridisation to the 18S rRNA probe. Before being reprobed filters were stripped by heating them to 95° C. in 0.1% SDS for 10 min.

mRNA stability: mRNA stability was determined by measuring abundance over a 2–12 h time period following the inhibition of transcription. Cells were grown to 70% confluence and transcription was inhibited by the addition of Actinomycin D (5 µg/ml). RNA was extracted as described above.

Polysome profiles and Translational Efficiency: Cells were grown to 70% confluency, scraped into the medium using a rubber policeman, then pelleted at 2000 rpm for 5 min. at 4 C. Cells were washed in DEPC PBS, and pelleted as before. The cells were resuspended in a solution of 10 mM TEA (triethanolamine) pH 7.6, 130 mM KCL, 5 mM $MgCl2$, 0.5 mM $CaCl2$, 0.25 mM sucrose with 0.5% deoxycholate and 0.5% Triton X100 incubated on ice 10 minutes. The nuclei were pelleted by centrifuging at 3000 rpm for 10 min at 4 C. 0.3 ml of the supernatant were loaded onto a 7 ml 15%–40% sucrose gradient and centrifuged at 200,000×g for 1 hour and then monitored by measuring the absorbance at 260 mm using a flow-through cell mounted in a Zeiss PM 2A spectrophotometer and coupled to a W+W recorder. The outflow from the flow cell was collected and each gradient split into three fractions—polysomes, monosomes, and remainder (untranslated material). Polysomes were pelleted by centrifuging at 32000×g for 17 hours and RNA was extracted from the pellet. Monosomal RNA was precipitated with isopropanol and ammonium acetate, then extracted as described earlier.

Results

Redirection of globin mRNA by albumin signal sequence: Initially, four plasmids were constructed based on the rabbit beta-globin 5'UTR and coding region together with either the native 3'UTR or the c-myc 3'UTR and both with and without the albumin signal sequence. These constructs were introduced into Ltk– fibroblasts and stable transfected cell lines were established. Expression of the transfected gene was assessed by Northern hybridisation to detect globin transcripts and all four genes were found to be expressed.

We found the highest levels of globin expression at 70% confluence (data not shown) and all subsequent experiments were carried out at that stage of growth.

Detergent/salt fractionation was carried out to investigate the compartmentation of the transcripts between FP,CBP and MBP. Each cell line was fractionated, polysomes pelleted, and then RNA extracted from the pellets and analysed by Northern hybridisation for abundance of globin transcripts. As shown in FIG. 2, in the control cell lines (GG) the globin transcript was found largely in free polysomes. In contrast, in cells expressing the globin transcript with the albumin signal sequence (SSGG) this transcript was found predominantly in the MBP/ER. The SSGM transcript was also found at highest abundance in the MBP/ER fraction.

Reprobing of filters with the 18S rRNA probe allowed correction for RNA loading and quantification of the hybridisation data per unit RNA. The abundance of globin transcripts in FP, CB and MBP was respectively $2.5\pm0.4$, $2.9\pm1.0$ and $2.1\pm0.9$ (means from at leased four separate experiments$\pm$s.e.m., expressed as arbitrary units of c.p.m. globin probe bound/c.p.m. 18S probe bound) in GG cells and 0.9—0.2, $1.3\pm0.2$ and $2.5\pm0.8$ in SSGG cells. Since it was the relative transcript distribution rather than overall expression level that was the most important parameter in these experiments, these data were then expressed relative to the abundance in FP fraction; as shown in FIG. 3 these data confirm that the addition of albumin signal sequence redirects the globin mRNA to the ER ($p=0.01$).

In the GM cells the abundance of globin transcripts in FP, CBP and MBP was respectively $2.6\pm0.7$, $2.8\pm0.9$ and $1.6\pm0.5$ (means from at leased four separate experiments$\pm$s.e.m., expressed as arbitrary units of c.p.m globin probe bound) and in SSGM cells the abundance distribution was respectively $2.5\pm1.1$, $2.3\pm0.8$ and $3.0\pm1.4$. Analysis of these data expressed as abundances relative to that in FP showed that the GM transcripts were present largely in CBP, as found previously in (Hesketh et al., 1994) but that, in contrast, the SSGM transcripts were found at similar relative abundances in CBP and MBP (FIG. 3). The abundance of globin transcripts in MBP was significantly greater in SSGM cells than in GM cells, again showing the ability of the signal sequence to redirect transcripts to the ER. However, the increased abundance in MBP in SSGM cells compared to GM cells was significantly less ($p<0.05$) than the increased abundance in SSGG cells compared to GG cells. Thus, although the signal sequence redirected the globin coding region and 5'UTR with the c-myc 3'UTR attached, the presence of both c-myc 3'UTR and the signal sequence reduced the extent to which redirection occurred. This suggests that there is competition between an ER localising signal (signal peptide) and a cytoskeletal localising signal (c-myc 3'UTR; Veyrune et al., 1996).

Addition of the signal sequence has no effect on mRNA stability or translational efficiency: Since it was theoretically possible that the manipulation of 5' signals may have altered the stability of the globin mRNA, we therefore determined the stability of the chimaeric transcripts. Each cell line was grown to 70% confluence and then treated with Actinomycin D to inhibit further transcription; RNA abundance was measured by Northern blotting. As globin is a highly stable message (Aviv et al., 1976) the abundance of GG and SSGG transcripts were measured over a 12 h period. As shown in FIG. 4, the addition al the albumin signal sequence did not significantly alter the stability of the globin mRNA. Similarly, analysis of GM SSGM cell lines showed that addition of the signal sequence to globin transcripts with the c-myc 3'UTR did not destabilise the nRNA (data not shown). Reprobing of the filters detect GAPDH nRNA indicated that transcription had been inhibited in all four cell lines (data not shown).

Effects of signal sequence on mRNA stability: Since it was theoretically possible that the manipulation of 5' and 3' signals may have altered the stability of the globin mRNA, we therefore determined the stability effect of the added signal sequence on mRNA stability. Cells were grown to 70% confluence and then treated with Actinomycin D to inhibit further transcription; RNA abundance was measured by Northern blotting. As globin is a highly stable message (Aviv et al, 1976) the abundance of GG and SSGG transcripts were measured over a 12 h period. As shown in FIG. 4, the addition of the albumin signal sequence did not significantly alter the stability of the globin mRNA. Reprobing of the filters to detect GAPDH mRNA (data not shown) indicated that transcription had been inhibited in both cell lines.

Translational efficiency: In order to determine whether the manipulation of signals within the foreign gene had affected either translation in general or translation of the modified gene in particular, the protein synthetic apparatus of the four cell lines was subjected to polysome profile analysis. The cells were lysed with salt and detergent, and soluble material loaded onto a 15%–40% sucrose gradient. Polysome profiles were recorded and are presented in FIG. 5, and polysome/monosome ratios in Table 2. Polysome profiles were very similar for all four lines with a similar proportion of ribosomes present in active polysomes. The different peak heights represent differences in the total amount of RNA loaded onto the gradient. Thus, transfection with the 4 constructs did not affect overall protein synthesis. Analysis of the proportion of globin transcripts in polysome and monosome fractions from the sucrose gradients (Table 3) shows that addition of the signal sequence did not significantly alter the translation of the transcripts.

The influence of the albumin 3'UTR: The results in FIG. 3 suggested that there is competition between 5' and 3' targeting signals but we were concerned that the observed effects were due to some form of interaction between the globin coding sequences and the c-myc 3'UTR which prevented the signal sequence performing its signalling role. To address this question we constructed a further vector with a different 3'UTR, namely the 3'UTR from the albumin gene: globin coding region with both the 3'UTR of rat albumin mRNA and the rat albumin signal sequence (SSGA). The plasmid was transfected into Ltk− cells and stable cell lines established. The SSGA cells were fractionated and analysed as described above. As shown in FIG. 6 the results show that the SSGA transcripts containing both albumin 3'UTR and signal sequence were recovered predominantly in the MBP/endoplasmic reticulum fraction. This indicates that introduction of a foreign 3'UTR is not sufficient, per se, to prevent redirection of the globin transcript to the ER. A further vector (GA) was made in which the globin coding sequence was linked to the rat albumin 3'UTR but without the signal sequence; unfortunately, further analysis was not possible because we were unable to detect transfected cells expressing this gene.

Discussion

The present results show that by a combination of DNA recombinant technology and transfection it is possible to produce cell lines in which the globin mRNA is retargeted to the endoplasmic reticulum. Thus, in Ltk− fibroblasts, the addition of the rat albumin signal sequence to globin with the native globin 3'UTR redirected the mRNA to membrane-bound polysomes. This is the first demonstration of redirection of a mRNA from free polysomes to the ER in a stable cell line. Partial redirection of histone mRNA to MBP has previously been demonstrated in mammalian cells (HeLa) using an *E. coli* signal sequence (Zambetti et al 1987). Also, Lee and co-workers (1996) have secreted active sialyltransferase from COS-7 cells using an IgM signal peptide but in this case the native sialyltransferase is synthesised in the ER. Importantly, in each of these cases, however, transfections were transient.

It is now clear that, in addition to mRNAs translated on free polysomes, a considerable proportion of mRNAs are translated in polysomes associated with the cytoskeleton (Hesketh, 1996). The targeting of mRNAs to the cytoskeleton has been shown to be due to signals in the 3'UTR (Hesketh et al, 1994; Veyrune et al, 1996; Mahon et al, 1997). As shown in FIG. 3, if in addition to a signal peptide, a cytoskeletal targeting signal is present in the 3'UTR of the transcript the shift to membrane-bound polysomes is decreased. This appears not to be caused by a non-specific effect of a 'foreign' 3'UTR because addition of a different 'foreign' 3'UTR, that from albumin, to globin (SSGA; FIG. 6) did not reduce the redirection by the signal sequence. The data indicate therefore that when a hybrid transcript contains both a signal sequence and a 3'UTR localisation signal there is a competition between the 5' and 3' signals. The c-myc 3'UTR localisation signal thus appears to interfere with mRNA sorting via a signal sequence.

These data have important implications for biotechnology. Firstly, they demonstrate that it is possible to create stable cell lines in which a mRNA coding for an intracellular protein is redirected to the ER. Secondly, they show that if such an mRNA contains a 3'UTR localisation signal then such a signal must be removed to achieve efficient redirection.

As indicated by the present results with the albumin 3'UTR (FIG. 6), it may be most appropriate to use a vector containing a 3'UTR from the mRNA for a secreted protein, particularly one form the same gene as the signal sequence being used; in this way the desired coding region is inserted between the 5'UTR/signal sequence and 3'UTR from an mRNA for a secreted protein and the problem of signal competition is abolished.

If such modified genes are to be used for commercial purposes, ideally the signal modification should not decrease mRNA stability and translational efficiency to any major extent. The data in FIGS. 4 & 5 show that addition of the signal sequence to globin had no effect on mRNA stability or translational efficiency. Thus, retargeting can be accompanied by a maintenance of mRNA stability and translation. Using luciferase as a reporter we have shown that retargeting of the mRNA by the albumin signal sequence is accompanied by synthesis of an immunologically recognizable protein in the ER.

In conclusion, the present results show that it possible to retarget an mRNA to the ER whilst maintaining stability and translation.

REFERENCES

Aviv, H., Valloch, V., Bastos, R., and Levy, S., (1976) Biosynthesis and stability of globin mRNA in cultured erythrolekemia fiend cells. Cell 8 495–503

Blobel, G. and Dobberstein, B. (1975) Transfer of proteins across membranes. I. Presence of proteolytically processed and unprocessed nascent immunoglobulin light chains on membrane-bound ribosomes of murine myeloma. J. Cell Biol. 67, 835–851.

Bock, S.C., Wion, K. L., Vehar, G. A., Lawn, R. M. (1982) Cloning and expression of the cDNA for human antithrombin III. Nuc. Acids Res. 10, 8113–8125.

Bonnieu, A., Piechaczyk, M., Marty, L., Cuny, M., Blanchard, J-M., Fort, P., Jeanteur, P. (1988) Sequence determinants of c-myc mRNA turnover: Influence of 3' and 5' non-coding regions. Oncogene Res. 3, 155–166.

Bonnieu, A., Roux, P., Marty, L., Jeanteur, P., Piechaczyk, M. (1990) AUUUA motifs are dispensible for rapid degradation of the mouse c-myc RNA. Oncogene 5, 1585–1588.

Chomczynski, P. and Sacchi, N. (1987) Single-step method of RNA isolation by acid guanidium thiocyanate-phenol-chloroform extraction. Anal. Biochem. 162, 156–159.

Devlin, J. J., Devlin, P. E., Myumbo, K., Lilly, M. B., Rado, T. A. Warren, M. K. (1987) Expression of granulocyte colony-stimulating factor by human cell lines. J. Leuk. Biol. 41, 302–306.

Garcia, C. K., Goldstein, J. L., Pathak, R. K., Anderson, R. G. W., Brown, M. S. (1994) Molecular characterisation of a membrane transporter for lactate, pyruvate, and other monocarboxylates: implications for the Cori cycle. Cell 76, 865–873.

Hesketh, J., Campbell, G., Piechaczyk, M., Blanchard, J-M. (1994 Targeting of c-myc and beta-globin sequences to cytoskeletal-bound polysomes by c-myc untranslated region. Biochem. J. 198, 143–148.

Hesketh, J. E. (1996) Intracellular sorting of macromolecules., Biochem. Soc. Trans. 24, 521–527.

Hovland, R., Campbell, G., Pryme, I., Hesketh, J. (1995) The mRNAs for cyclin A, c-myc and ribosomal proteins L4 and S6 are associated with cytoskeletal-bound polysomes in HepG2 cells. Biochem. J. 310, 193–196.

Hovland, R., Hesketh, J. E., Pryme, I. F. (1996) The compartmentalisation of protein synthesis: importance of cytoskeleton and role in mRNA targeting. Int. J. Biochem. Cell Biol. 28, 1089–1105.

James, J., and Simpson, B. K., (1996) Application of enzymes in food processing. Crit. Rev. Food Sci. Nutr. 36, 437–463

Kislauskis, E. H., Zhu, S., Singer, R. H. (1994) Sequences responsible for intracellular localisation of beta-actin messenger RNA also affect cell phenotype. J. Cell Biol. 127, 441–451.

Lee, Y-C., Kim, C-H., Tsuji, S. (1996) An efficient expression vector for extracellular secretion in mammalian cells. Mol. Cells 6, 552–556.

Lin, F-K., Lin, C-H., Lai, P-H., Browne, J. K., Egrie, J. C., Smalling, R., Fox, J. M., Chen, K. K., Castro, M., Suggs, S. (1986) Monkey erythropoietin gene: cloning, expression and comparison with the human erythropoietin gene. Gene 44, 201–209.

Mahon, P., Beattle, J., Glover, L. A., Hesketh, J. (1995) Localisation of metallothionein isoform mRNAs in rat hepatoma (H4) cells. FEBS Letters 373, 76–80.

Michel, M-L., Sobczak, E., Malpiece, Y., Tiollais, P., Streeck, R. E. (1985) Expression of amplified hepatitis B virus surface antigen genes in Chinese hamster ovary cells. Bio/Technology 3, 561–566.

Pryme, I. F., Partridge, K., Johannessen, A. J., Jodar, D., Tauler, A., Hesketh, J. E. (1996) Compartmentation of the protein synthetic machinery into free, cytoskeletal-bound and membrane-bound polysomes. Genetic Engineer and Biotechnologist [need correct abbreviation] 16, 137–144.

Sambrook, J., Fritisch, E. F., Maniatis, T. (1989) Molecular Cloning: a laboratory manual (2nd ed), Cold Spring Harbor Laboratory Press.

Shak, S., Capon, D. J., Hellmiss, R. Marsters, S. A., Baker, C. L. (1990) Recombinant human DNase I reduces the viscosity of cystic fibrosis sputum. Proc. Nat. Acad. Sci. USA 87, 9188–9192.

Vedeler, A., Pryme, I. F., Hesketh, J. E. (1991) The characterization of free, cytoskeletal and membrane-bound polysomes in KrebII as cited and 3T3 cells. Mol. Cell Bioch. 100, 183–193.

Veyrune, J-L., Campbell, G. P., Wiseman, J., Blanchard, J-M., Hesketh, J. E. (1996) A localisation signal in the 3' untranslated region of c-myc mRNA targets c-myc mRNA and beta-globin reporter sequences to the perinuclear cytoplams and cytoskeletal-bound polysomes. J. Cell Science 109, 1185–1194.

Wilson, I. A., Brindle, K. M., Fulton, A. M. (1995) Differential localisation of the mRNAs of the M and B isoforms of creating kinase in myoblasts. Biochem. J. 308, 599–605.

Zambetti, G., Stein, G., and Stein, J. (1987) Targeting of a chimaeric human histone fusion mRNA to membrane-bound polysomes in HeLa cells. Proc. Natl. Acad. Sci. USA 84, 2683–7

TABLE 1

Oligodeoxynucleotides For PCR

KP4-GAC AAG CTG CAC GTG GAT CCT GAG AAC TTC

KP5-AAA AGA AAA CtC TaG aTG GCC CAA TTG TAT

KP6-GGA CTT TCC AAA ATC TCG TAA CAA CTC CGC

KP7-CTG GAC AGA TGC ACc atA TGG TCT GTT TTG

KP8-GAA GTT CTC AGG ATC CAC GTG CAG CTT GTC

Table 1. Oligos used in cloning the various expression vectors described in the text. (SEQ ID NO's: 1–5). Letters in lowercase represent changes required to create restriction sites.

TABLE 2

|      | Polysomes      | Monosomes      |
|------|----------------|----------------|
| GG   | 56.5% ± 3.0    | 43.5% ± 3.0    |
| SSGG | 53.9% ± 1.7    | 46.1% ± 1.7    |
| GM   | 51.7% ± 0.4    | 48.3% ± 0.4    |
| SSGM | 51.7% ± 1.1    | 48.3% ± 1.1    |

Table 2. Distribution of ribosomes in Polysomes and Monosomes. Percentage distribution of ribosomes was calculated from the amounts of $A_{260}$-absorbing material present in polysomes and monosomes separated by sucrose density gradient centrifugation. Results are means±S.E.M. (n=6 for GG and SSGG, n=9 for GM and SSGM).

TABLE 3

|      | Polysomes | Monosomes |
|------|-----------|-----------|
| GG   | 32.3%     | 67.7%     |
| SSGG | 42.1%     | 57.9%     |
| GM   | 57.8%     | 42.2%     |
| SSGM | 48.5%     | 51.5%     |

Table 3. Distribution of globin transcript in polysomes and monosomes. RNA was extracted from polysome and monosomes fractions recovered from sucrose density gradients (profiles shown in FIG. 5) and analysed for globin mRNA abundance by Northern Blotting.

---

What is claimed is:

1. A nucleic acid molecule encoding a mammalian signal peptide operatively linked to a nucleic acid encoding a protein that would normally not be secreted from a mammalian cell, said signal peptide allowing at least some of said protein to be synthesized on the endoplasmic reticulum in a manner so that said protein can be secreted, the nucleic acid molecule comprising an insertion, or substitution with respect to all or part of a 3' untranslated region, relative to the corresponding region present in naturally occurring RNA encoding said protein, such that the region's effect in directing molecules to an intracellular location other than the endoplasmic reticulum or to free and/or cytoskeletal bound polysomes is eliminated or reduced relative to the corresponding naturally occurring sequence.

2. The nucleic acid molecule of claim 1, which is DNA.

3. The nucleic acid molecule of claim 1, which is RNA.

4. The nucleic acid molecule of claim 1, wherein said signal peptide is a signal peptide normally from a protein which is secreted from mammalian cells.

5. The nucleic acid molecule of claim 4, wherein said protein which is secreted from mammalian cells is a growth hormone, a milk protein or albumin.

6. A vector comprising the nucleic acid molecule of claim 1.

7. A mammalian cell comprising the nucleic acid molecule of claim 1.

8. A method of obtaining a protein from a cultured mammalian cell which has been transfected with the nucleic acid of claim 1, comprising expressing the protein in the cell, allowing the cell to secrete the protein and purifying the protein.

9. A nucleic acid molecule encoding a mammalian signal peptide operatively linked to a nucleic acid encoding a protein that would normally not be secreted from a mammalian cell, said signal peptide allowing at least some of said protein to be synthesized on the endoplasmic reticulum in a manner so that said protein can be secreted, wherein said nucleic acid molecule comprises an entire 3' untranslated region from a nucleic acid encoding a secreted protein substituted for the entire native 3' untranslated region of said protein normally not secreted, such that said substituted region's effect in directing molecules to an intracellular location other than the endoplasmic reticulum or to free and/or cytoskeletal bound polysomes is eliminated or reduced relative to that obtained with the native 3' untranslated region.

10. A vector comprising a signal sequence operatively linked to a nucleotide sequence coding for a mammalian protein operatively linked to a 3' UTR, wherein said signal sequence and said 3' UTR are from an mRNA for a secreted protein which is different to the mammalian protein coded for by said nucleotide sequence.

11. The vector of claim 10, wherein the signal sequence and the 3' UTR are from the same protein.

12. The vector of claim 10 or 11, wherein the mammalian protein coded for by said nucleotide sequence is not normally secreted.

13. A nucleic acid molecule encoding a mammalian signal peptide operatively linked to a nucleic acid encoding a protein that would normally not be secreted from a mammalian cell, said signal peptide allowing at least some of said protein to be synthesized on the endoplasmic reticulum in a manner so that said protein can be secreted, the nucleic acid molecule comprising a deletion with respect to part of a 3' untranslated region from a nucleic acid encoding a secreted protein substituted for the corresponding 3' untranslated region present in naturally occurring RNA encoding said protein, such that the region's effect in directing molecules to an intracellular location other than the endoplasmic reticulum or to free and/or cytoskeletal bound polysomes is eliminated or reduced relative to the corresponding naturally occurring sequence.

14. The nucleic acid molecule of claim 13 which is DNA.

15. The nucleic acid molecule of claim 13 which is RNA.

16. The nucleic acid molecule of claim 13, wherein said signal peptide is a signal peptide normally from a protein which is secreted from mammalian cells.

17. The nucleic acid molecule of claim 16 wherein said protein which is secreted from mammalian cells is a growth hormone, a milk protein or albumin.

18. A vector comprising the nucleic acid molecule of claim 13.

19. An isolated mammalian cell comprising the nucleic acid molecule of claim 13, wherein said cell is in a cell culture.

20. A method of obtaining a protein from a mammalian cell, comprising expressing the protein in the cell using the nucleic acid of claim 13, allowing the cell to secrete the protein and purifying the protein.

* * * * *

SEQUENCE LISTING

<160> NUMBER OF SEQ ID NOS: 5

<210> SEQ ID NO 1
<211> LENGTH: 30
<212> TYPE: DNA
<213> ORGANISM: Artificial Sequence
<220> FEATURE:
<223> OTHER INFORMATION: Oligonucleotide used in cloning various
      expression vectors

<400> SEQUENCE: 1
gacaagctgc acgtggatcc tgagaacttc                                    30

<210> SEQ ID NO 2
<211> LENGTH: 30
<212> TYPE: DNA
<213> ORGANISM: Artificial Sequence
<220> FEATURE:
<223> OTHER INFORMATION: Oligonucleotide used in cloning various
      expression vectors

<400> SEQUENCE: 2
aaaagaaaac tctagatggc ccaattgtat                                    30

<210> SEQ ID NO 3
<211> LENGTH: 30
<212> TYPE: DNA

-continued

```
<213> ORGANISM: Artificial Sequence
<220> FEATURE:
<223> OTHER INFORMATION: Oligonucleotide used in cloning various
      expression vectors

<400> SEQUENCE: 3
ggactttcca aaatctcgta acaactccgc                                          30

<210> SEQ ID NO 4
<211> LENGTH: 30
<212> TYPE: DNA
<213> ORGANISM: Artificial Sequence
<220> FEATURE:
<223> OTHER INFORMATION: Oligonucleotide used in cloning various
      expression vectors

<400> SEQUENCE: 4
ctggacagat gcaccatatg gtctgttttg                                          30

<210> SEQ ID NO 5
<211> LENGTH: 30
<212> TYPE: DNA
<213> ORGANISM: Artificial Sequence
<220> FEATURE:
<223> OTHER INFORMATION: Oligonucleotide used in cloning various
      expression vectors

<400> SEQUENCE: 5
gaagttctca ggatccacgt gcagcttgtc                                          30
```